United States Patent [19]

Gillis, Jr.

[11] Patent Number: 4,816,600

[45] Date of Patent: Mar. 28, 1989

[54] ISOCYANATE COMPOSITIONS OBTAINED FROM REACTION OF ISOCYANATES WITH BLOCKED POLAMINES

[75] Inventor: Herbert R. Gillis, Jr., West Depford, N.J.

[73] Assignee: ICI Americas Inc., Wilmington, Del.

[21] Appl. No.: 97,308

[22] Filed: Sep. 14, 1987

Related U.S. Application Data

[63] Continuation of Ser. No. 764,435, Aug. 9, 1985, abandoned.

[51] Int. Cl.$^4$ .......................................... C07C 127/24
[52] U.S. Cl. ..................................... 560/335; 564/38; 564/50
[58] Field of Search ...................... 564/38, 50; 560/335

[56] References Cited

U.S. PATENT DOCUMENTS

| | | |
|---|---|---|
| 3,441,588 | 4/1969 | Wagner et al. ...................... 560/335 |
| 3,903,127 | 9/1975 | Wagner et al. ...................... 560/335 |
| 3,976,622 | 8/1976 | Wagner et al. ...................... 560/335 |
| 4,136,241 | 1/1979 | Ammann ............................. 521/163 |
| 4,340,712 | 7/1982 | Reichmann et al. ................ 560/335 |
| 4,373,080 | 2/1983 | Reichmann et al. .................. 528/45 |
| 4,386,218 | 5/1983 | Rasshofer et al. .................... 564/38 |
| 4,645,630 | 2/1987 | Rasshofer et al. .................... 264/54 |

FOREIGN PATENT DOCUMENTS

| | | | |
|---|---|---|---|
| 0012970 | 12/1979 | European Pat. Off. . | |
| 0050275 | 4/1982 | European Pat. Off. .............. | 564/38 |
| 0135867 | 9/1984 | European Pat. Off. . | |
| 739068 | 6/1980 | U.S.S.R. ................................ | 564/50 |

*Primary Examiner*—Glennon H. Hollrah
*Assistant Examiner*—John A. Sopp
*Attorney, Agent, or Firm*—James T. Jones

[57] ABSTRACT

Modified organic isocyanate composition containing urea and/or biuret groups and/or salts of these groups, obtained from the reaction of a blocked polyamine composition and an unblocked isocyanate composition.

43 Claims, No Drawings

ISOCYANATE COMPOSITIONS OBTAINED FROM REACTION OF ISOCYANATES WITH BLOCKED POLAMINES

This is a continuation of copending application Ser. No. 764,435, filed on Aug. 9, 1985, now abandoned.

The invention relates to organic polyisocyanate compositions which contain urea, biuret, or a mixture of biuret and urea structures, and to methods for preparing said compositions, which are liquid at ambient temperatures.

BACKGROUND

Biuret modified isocyanate compositions have long been known in the polyurethane industry. German Pat. No. 1,101,394 contains examples in which biuret modified isocyanates are prepared via partial saponification (with $H_2O$ or $H_2S$) of isocyanate while heating. The biuret structures are formed in a two step reaction sequence. The initial saponification reaction leads to the formation of urea linkages. Under the influence of heat these ureas will further react to form biuret structures:

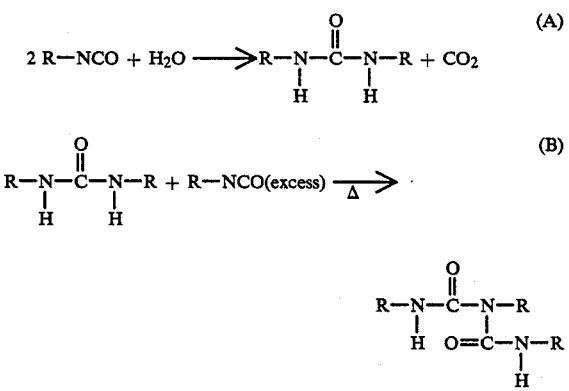

plus higher order biuret structures.

This technique is effective because step A is a relatively slow reaction, such that the intermediate urea is consumed (in step B) at a rate which is comparable to its rate of formation. Moreover the active hydrogen species ($H_2O$ or $H_2S$) has sufficient time to diffuse throughout the isocyanate before reacting, such that the reaction proceeds evenly throughout the bulk of the sample.

Biuret modified isocyanates may also be prepared via the reaction of mono or polyamines with polyisocyanates at sufficiently elevated temperatures. Here also, the reaction sequence involves two steps:

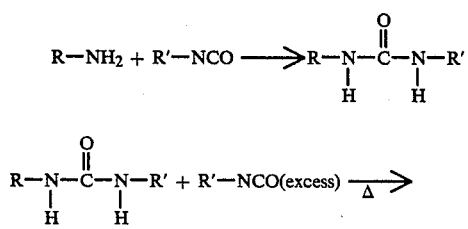

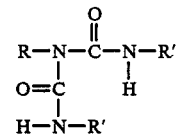

plus higher order biuret structures.

This technique is generally not satisfactory because step C is a veyy fast reaction, such that the starting amine is unable to diffuse into the bulk of the isocyanate before reacting. Thus the bulk of the reaction in step C occurs at the point of mixing between the amine and the isocyanate and produces a very high concentration of urea intermediate at the point of mixing. In the vast majority of cases this concentration effect results in the formation of solid precipitates. These urea precipitates must be redissolved before biuret formation (step D) can occur. This resolubilization can be accomplished by heating and vigorous agitation, but the temperatures required are generally rather extreme (usually >150° C.), and much higher than is needed to promote biuretization (step D). The use of such high temperatures is uneconomical and can result in undesirable side reactions. These side reactions can lead to product discoloration and, in some cases, to the liberation of volatile and toxic by-products (via a series of biuret exchange reactions).

Several methods have been developed to overcome the problems of solids formation, discussed above. By far the oldest and most straightforward method for avoiding the formation of urea precipitates is to conduct the entire reaction in an appropriate solvent. Generally, however, the use of solvents is impractical for economic and environmental reasons. According to the teachings of U.S. Pat. No. 4,147,714, it is possible to prepare biuret modified isocyanate compositions by reacting a liquid isocyanate with an amine vapor. The use of a vapor greatly increases the surface area of the reaction interface between the amine and isocyanate—thereby eliminating high local concentrations of insoluble urea intermediates. Similarly, the precipitation of insoluble polyurea intermediates can be eliminated, according to U.S. Pat. No. 3,824,266, by using amines which are slow-reacting (i.e., sterically or electronically deactivated). Presumably this "deactivation" permits the amine to diffuse into the bulk isocyanate before reacting—thereby increasing the size of the reaction interface. Finally, U.S. Pat. No. 3,441,588 teaches that biuret prepolymers may be conveniently prepared, without the undesirable formation of solid urea precipitates, by employing a high molecular weight polyether diamine in the reaction with isocyanates. It appears likely that the long polyether chain acts as an internal "solvent" for the intermediate urea, thereby inhibiting phase separation. In spite of the "solvent" effect of the polyether chain, it is generally not possible to prepare analogous biuret modified isocyanate compositions from polyether polyamines having reactive amine functionalities of greater than 2 (i.e., polyether triamines), without using inert solvents or extreme reaction conditions (i.e., temperatures of much greater than 100° C). These fast-reacting high functionality amines can react with the isocyanate, crosslink, and gel before diffusing into the bulk of the isocyanate sample. This problem is most severe in the more reactive (aromatic) polyisocyanates, such as MDI. Gelation and separation problems may also be encountered when attempting to react polyether diamines with isocyanates having functionality greater than 2.

Much of the interest in biurets, as modifying additives for isocyanates, stems from the poor solubility of the corresponding urea systems. Biuretization substantially increases solubility—perhaps by interfering with the formation of hydrogen bond networks and oligomers. Whereas all of the patent documents cited thus far pertain specifically to biuret modified isocyanate compositions, U.S. Pat. No. 3,943,158 pertains to urea modified compositions. These urea prepolymers are formed by the reaction of diisocyanates with certain bis-secondary diamines. The use of secondary amines undoubtedly interferes with the formation of hydrogen bond networks in a manner which is closely analogous to that of biuretization.

SUMMARY OF THE INVENTION

The urea, biuret, or mixed urea/biuret modified isocyanate compositions described herein have many potential applications. These types of modification are particularly valuable for preparing liquid low, and medium functionality derivatives of diphenylmethane diisocyanate (MDI) which are free of urethane linkages. A principal object of this invention is modified isocyanate compositions which contain significant quantities of urea and/or biuret structures. A further object of the invention is urea and/or biuret modified isocyanate compositions obtained from the reaction of latent (blocked or retarded) polyamines of amine functionality greater than 2, with polyisocyanates. A still further object of the invention is urea and/or biuret modified isocyanate compositions obtained from the reaction of latent (blocked or retarded) polyamines of amine functionality greater than about 1, with polyisocyanates having number averaged isocyanate (NCO) functionalities of greater than 2. A still further object of the invention is urea and/or biuret modified isocyanate compositions obtained from the reaction of latent (blockdd or retarded) polyamines with polyisocyanates at low temperatures (i.e., 50° C. or less) using an in-line or impingement mixing technique. Yet further objects of the invention include urea and/or biuret modified isocyanate compositions, of the types described hereinabove, which are substantially free of urethane linkages and which are liquid and stable to storage at ambient temperatures. A further object of the invention is polyurea, polyurethane, and polyurethanurea polymers (i.e., plastics materials) derived from the aforementioned urea and/or biuret modified isocyanate compositions; and methods of preparing said polymers.

It has now surprisingly been found that isocyanate compositions which contain significant quantities of urea and/or biuret terminated structures may be prepared quite conveniently by rapid mixing of certain blocked or "retarded" polyamines with polyisocyanates. The reactions may be performed at low temperatures (i.e., ambient, or slightly above). When appropriate blocking or retarding agents are used, the functionalities of the reagents (amine and/or isocyanate) may be higher than 2. The use of high-functionality reagents, either individually or in combination, does not necessitate any increase in the severity of the reaction condition (i.e., the temperature of reaction). This represents a very significant improvement, in processing convenience, over prior art methods. Modified isocyanate compositions which have previously been inaccessible or impractical may now be prepared with surprising ease. Most of the modified isocyanate compositions prepared from the blocked or "retarded" polyamines, and isocyanates (even the highest functionality combinations) exhibit surprising homogeneity and stability at ambient temperatures. The compositions are generally clear, free of solids, and low in viscosity.

Suitable blocking or "retarding" agents which may be used with polyamines include anhydrous acids such as HCl, HBr, HI, sulfonic acids, and carboxylic acids which will form salts with the polyamine:

These salts will react with polyisocyanates to form urea and/or biuret structures, but this reaction proceeds much more slowly than that of the corresponding free amines. This permits the salt time to diffuse into the substrate isocyanate before it reacts thereby reducing the chances of premature gelation. The stronger the acid, the more effective the reactivity moderating (retarding or blocking) effect. It is, therefore, desirable to use the stronger acids in order to "block" the highest functionality polyamines.

Other suitable blocking agents include silylating agents such as trimethylsilylnitrile, trimethylsilylazide, etc. or alkylating agents which will convert primary amine terminated polyethers into various kinds of secondary amine species. For example:

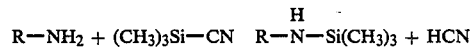

It is preferred that these permanent blocking agents be of the type which will hinder the reaction of the secondary amine groups with isocyanates by stearic "crowding." Any suitable blocking agent may be used, whether labile or permanent, provided that it retards the reaction of the polyamine with the polyisocyanate sufficiently well to permit adequate mixing, without preventing eventual reaction of these ingredients after mixing. In some cases, it is possible to use very mild, labile retarding agents such as $CO_2$, $CS_2$, $SO_2$, and like species which will complex reversably with amines.

DETAILED DESCRIPTION OF THE INVENTION

Polyamines which are suitable for blocking or "reactivity modification", for preparing the urea and/or biuret modified isocyanate compositions of the invention, are preferably those having a primary and/or secondary number averaged amine functionality of at least 1. Many useful di and trifunctional primary amine terminated polyethers and methods for their preparation, are as described in U.S. Pat. Nos. 3,236,895; 3,441,588; and 3,654,370. The disclosures of these patents are incorporated herein by reference. Preferred compositions include primary and/or secondary amine containing polyamines having number averaged amine functionalities of between about 2 and about 6 and having amine equivalent weights above about 100. The term "number averaged amine functionality" is used to refer to the average number of primary and secondary amino groups in an average polyamine molecule. These amine compositions may be single compounds or mixtures of compounds. Said mixtures may include amines of more than one structural type and functionality. Said mixtures may also include polyols, which are substantially free of amine functionality, provided that the number averaged amine functionality of the mixtures is as described hereinabove. The number averaged amine functionality of said mixtures, as defined above, may be calculated using the following formula I:

$$F_A = \left( \sum_{i=1}^{i=m} \left[ \frac{F_i n_i}{MW_i} \right] \right) \bigg/ \left( \sum_{i=1}^{i=m} \left[ \frac{n_i}{MW_i} \right] \right) \quad (I)$$

wherein $F_A$ = a Number Averaged Amine Functionality of Mixture m = Number of distinct molecular species, in the mixture which contain active hydrogen groups ni = The weight of the ith molecular component of the mixture Fi = The number of reactive amine groups (Primary and Secondary amines) in the ith molecular component of the mixture.

MWi = The molecular weight of the ith component of the mixture.

It is to be understood that each of the amine containing molecular components of the compositions described hereinabove may be based on a variety of chemical monomers units. These units may, for example, include polyethers, thioethers, esters, phosphates, silanes, siloxanes, urethanes, hydrocarbon sequences, and the like. It is to be understood, further, that each of the individual molecular components of the compositions described hereinabove may contain other types of active hydrogen containing groups, in addition to the primary and/or secondary amine groups. These additional active hydrogen containing units may, for example, include hydroxyl groups, phenol groups, carboxylic acid groups, thiol groups, and the like.

The amino functional compositions useful in the practice of the instant invention may contain secondary in addition to or instead of primary amino groups. These reactive amino groups, whether primary and/or secondary, may be either aliphatically bound, or aromatically bound, or a mixture of both types.

Examples of commercial amine terminated polyethers which are preferred for use in the instant invention include JEFFAMINE® D-4000, a 4000 molecular weight primary amine terminated polypropylene oxide diamine; JEFFAMINE® D-2000, a 2000 molecular weight primary amine terminated polypropylene oxide diamine; JEFFAMINE® T-5000, a 5000 molecular weight primary amine terminated polypropylene oxide triamine; JEFFAMINE® T-3000, a 3000 molecular weight primary amine terminated polypropylene oxide triamine; JEFFAMINE® ED-2001, a 2000 molecular weight primary amine terminated polyoxypropylene polyoxyethylene copolymer diamine; and JEFFAMINE® ED-600, a 600 molecular weight primary amine terminated polyoxypropylene polyoxyethylene copolymer diamine; or mixtures thereof.

A wide variety of aromatic and/or aliphatic polyisocyanates may be used. Typical aromatic polyisocyanates include p-phenylene diisocyanate, polymethylene polyphenylisocyanate, 2,6-toluene diisocyanate, dianisidine diisocyanate, bitolylene diisocyanate, naphthalene-1,4-diisocyanate, bis(4-isocyanatophenyl)methane, bis(3-methyl-4-isocyanatophenyl)methane, and 4,4'-diphenylpropane diisocyanate.

Other aromatic polyisocyanates used in the practice of the invention are methylene-bridged polyphenyl polyisocyanate mixtures which have a functionality of from about 2 to about 5. These latter isocyanate compounds are generally produced by the phosgenation of corresponding methylene bridged Polyphenyl polyamines, which are conventionally produced by the reaction of formaldehyde and primary aromatic amines, such as aniline, in the presence of hydrochloric acid and/or other acidic catalysts. Known processes for preparing polyamines and corresponding methylene bridged polyphenyl polyisocyanates therefrom are described in the literature and in many patents, for example, U.S. Pat. Nos. 2,683,730: 2,950,263; 3,012,008; 3,344,162 and 3,362,979.

Pure diphenylmethane diisocyanates (in particular, the 4,4'-isomer; 2,4'-isomer: 2,2'-isomer and mixtures thereof) are obtained by distillation and/or crystallization from crude mixtures of methylene bridged polyphenyl polyisocyanates.

By far the most preferred aromatic polyisocyanate is methylene bis(4-phenylisocyanate) or MDI. Pure MDI, quasi-prepolymers of MDI, modified pure MDI, etc. Since pure MDI is a solid and, thus, often inconvenient to use, liquid products based on MDI are often used and are included in the scope of the terms MDI or methylene bis(4-phenylisocyanate) used herein. U.S. Pat. No. 3,394,164 contains an example of a liquid MDI product. Uretonimine modified pure MDI may be used. This product is made by heating pure distilled MDI in the presence of a catalyst. The liquid product is a mixture of pure MDI and modified MDI:

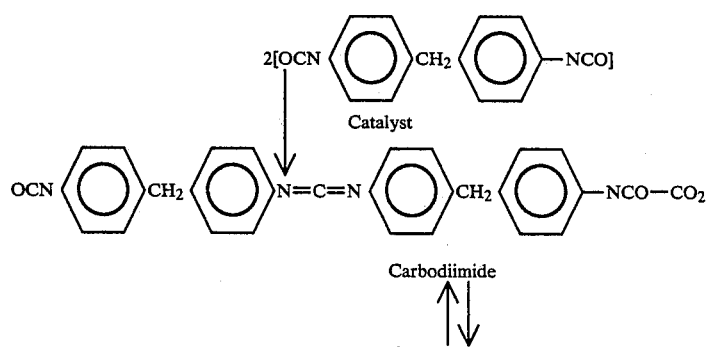

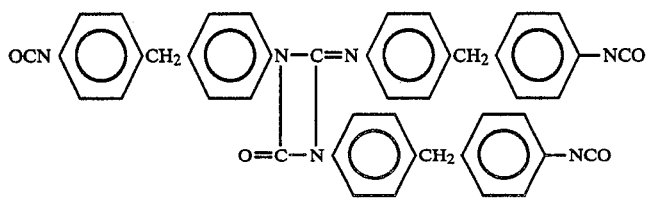

Uretonimine

Example of commercial materials of this type are Rubinate-44; Rubinate LF-168; Rubinate XI-208; experimental diisocyanate composition 4397-49 (approximately an 80:20 mole/mole blend of 4,4'-diphenylmethane diisocyanate with 2,4'-diphenylmethane diisocyanate, which also contains minor amounts of 2,2'-diphenylmethane diisocyanate); or mixtures of the above; all from Rubicon Chemicals Inc. Of course, the terms polyisocyanate also includes quasi-prepolymers of polyisocyanates with polyols. Example of such materials are Rubinate LF-179 and Rubinate LF-167 (prepolymer modified MDI products); also available from Rubicon Chemicals Inc.

A wide variety of aliphatic isocyanates may also be used in accordance with this invention. Illustrative examples of such isocyanates include 1,6-hexamethylene diisocyanate, ethylene diisocyanate, cyclopentylene-1,3-diisocyanate, and diisocyanato dicyclohexyl methane.

Any of the polyisocyanate compositions described hereinabove, or any mixture thereof, may be regarded as a suitable substrate (or "base isocyanate") for urea/biuret modification within the scope of the instant invention. Further examples of suitable base isocyanate compositions, which are available commercially, include Rubinate M, Polymeric polyphenylmethane polyisocyanate from Rubicon Chemicals; Rubinate MF-182 and Rubinate MF-185, modifed polymeric polyphenylmethane polyisocyanates also from Rubicon Chemicals Inc.: or mixtures thereof.

Suitable blocking or retarding, or "reactivity modifying" agents, for use with the aforementioned polyamines, include any anhydrous proton acid. Particularly suitable proton acids include hydrohalic acids such as hydrofluoric, hydrochloric, hydrobromic, or hydroiodic acids; lower molecular weight carboxylic acids such as acetic acid, propionic acid, benzoic acid, adipic acid, terephthalic acid, trifluoroacetic acid, trichloroacetic acid, carbonic acid, hydroxyacetic acid, acrylic acid, methacrylic acid, oxalic acid, malonic acid, fumaric acid, succinic acid, mixtures thereof, and the like; sulfonic acids such as methanesulfonic acid, benzenesulfonic acid, toluenesulfonic acid, trifluoromethane sulfonic acid, polystyrene sulfonic acid(s), and mixtures thereof; phosphonic acids such as phenylphosphoric acid, methylphosphonic acid, butylphosphonic acid, and the like. In some instances it may be acceptable to use the mineral oxyacids such as sulfuric acid, boric acid, nitric acid, nitrous acid, sulfurous acid, phosphoric acid, arsenic acid, silicic acid, and like materials; provided that these are substantially free of water and can be made compatible with the polyamine composition. In some instances it may be possible to employ blocking or retarding agents which are essentially aprotic but which will form labile complexes with the polyamine. These species include $CS_2$, $CO_2$, $SO_2$, $SO_3$, etc.; and Lewis acids such as inorganic or organic salts of magnesium, calcium, aluminum, iron, manganese, cobalt, zinc, lithium, boron, etc. Some specific examples of the Lewis acidic materials include zinc propionate, calcium sulfate and hydrates thereof, magnesium acetate and hydrates thereof, magnesium chloride and its hydrates, triphenylboron, hydrated alumina, ferric chloride, and the like. Finally, it is in many instances possible to use blocking or retarding agents which are essentially permanent in nature, in the sense that their action results in the conversion of primary amines into, slower reacting, secondary amines. These permanent blocking agents will remain associated with the nitrogen atoms of the polyamine even after these nitrogen atoms have been reacted with isocyanates—to form the urea and/or biuret modified compositions of the invention. Such permanent blocking agents include silylating agents such as trimethylsilyl chloride, triethylsilyl bromide, trimethylsilylnitrile, trimethylsilylazide, t-butyldimethylsilyl chloride, trimethylsilyl imidazole, trimethylsilane, and like materials; various organic alkylating agents such as t-butyl chloride, acrylonitrile, acrylamide, methyl methacrylate, dimethyl fumarate, butyl acrylate, isopropyl cinnamate, diphenylmethyl chloride, triphenylmethyl chloride, 1-chloroethylbenzene, 1-bromopropylbenzene, neopentyl bromide, and like materials or mixtures of such materials. It may, in some instances, be acceptable to use organometallic blocking agents such as trimethylgermanyl chloride, tributylstannyl chloride, triethyl borate, tri-n-butyl silicate, dicyclopentadienyltitanium dichloride, dicyclopentadienylniobium trichloride, mercuric acetate, and similar materials.

The choice of a blocking agent will depend upon a large number of factors, such as cost, availability, solubility in the polyamine, the degree of difficulty involved in preparing the blocked polyamine, storage stability of the blocked amine, etc. In all cases, however, it is critical that the blocking or retarding agent be chosen so as to reduce the reactivity of the amine towards isoycanates, without actually preventing this reaction. The blocked polyamines must eventually react to form urea and/or biuret structures, in the presence of organic isocyanates. Accordingly, blocking agents or conditions which result in the formation of tertiary amine or quaternary ammonium species must be avoided because these types of amine derivatives cannot form urea and/or biuret species, in the presence of isocyanates. When alkylating or metallating agents are used, the agent itself and the reaction conditions must be chosen in such a way as to limit polyalkylation or polymetallation of the amine nitrogen atoms. It is, therefore, preferred that the number of reactive equivalents of alkylating or metallating agents used should be less than or equal to the number of equivalents of reactive primary amines present in the substrate polyamine(s). It is preferred, further, that the alkylating or metallating agents be chosen so as to provide, subsequent to reaction with the amine, a degree of steric hinderance in order to inhibit a second alkylation or metallation at the same position(s). Alkylating or metallating agents which provide steric bulk at the site of reaction are greatly preferred over those which do not. Bulky agents such as trimethylsilylnitrile are preferred over smaller alkylating agents such as methyl iodide. When labile blocking agents are used, such as the acids described hereinabove, it is preferred that the number of reactive equivalents of blocking agents used be less than or equal to the number of reactive equivalents of primary and secondary amines present in the polyamine substrate composition. If an excess of the labile blocking agent is used, relative to the quantity of amine groups present, then it is preferred that some provision should be made for removal or neutralization of the excess blocking agent subsequent to the blocking reaction.

When choosing blocking agents, whether permanent or labile, the compatability of the blocking agent and/or the blocked polyamine and/or the ultimate decomposition products of the blocking agent with the isocyanate substrate composition must be allowed for. In particular, it is greatly preferred that the storage stability and the ultimate reactivity of the urea and/or biuret modified isocyanate compositions of the invention not be compromised by impurities introduced from the blocking operation. It is further preferred that these impurities not result in the prolonged evolution of toxic or obnoxious by-products from the urea and/or biuret modified isocyanate compositions. The choice of blocking agent is therefore partly dependent upon the properties or characteristics of the final urea and/or biuret modified compositions, and of polymeric compositions derived therefrom. Many of these properties or characteristics are end-user dependant and, as such, are somewhat subjective.

The process for preparing the blocked or "reactivity modified" polyamine compositions may, in the most preferred embodiment, be conducted in the absence of any solvents. When carrying out this most preferred process, the solubility of the blocking or "reactivity modifying" agent in the substrate polyamine composition must be allowed for, since otherwise a phase separation will likely result. The process may, if desired, be conducted using solvents which are largely inert towards the blocking agent and the substrate polyamine composition. The choice of solvents will depend to a large extent upon the type of blocking agent used. In general, the solvent should not interfere with the blocking reaction or with the stability of the blocked amine product. Depending upon the system, it may be possible and desirable to use protic solvents such as water, alcohols, polyols, carboxylic acids, inorganic acids, sulfonic acids, amides, and the like. In most cases it will be necessary to use aprotic solvents such as hydrocarbons, ethers, polyethers, esters, halocarbons, alkylated amides, alkylated ureas, sulfoxides, and like materials. Both the blocking agent and the polyamine substrate must be soluble, to some extent, in the chosen solvent. Solvents are particularly useful when the compatability between the blocking agent and the polyamine substrate composition is poor. The solvents may be used to dilute either the blocking agent, the polyamine substrate, or both.

According to the more preferred (i.e., solvent free) embodiments of the invention, the blocking agent and the polyamine substrate composition are combined and mixed in appropriate amounts, along with any appropriate catalysts, in a chemical reactor and heated to a temperature and pressure which are sufficient to promote the desired blocking reaction. The resulting mixture is agitated until the reaction has reached the desired degree of completion. According to the most preferred embodiments, the "chemical reactor" is simply a static (in-line) mixer or an impingement mixing apparatus into which the reagent streams are fed at a rate, temperature, pressure, and weight ratio which is most appropriate for the desired blocking reaction. Under this, most preferred, processing arrangement, the need for bulky processing equipment and for lengthy synthetic operations is largely eliminated.

The process for preparing the urea and/or biuret modified isocyanate compositions may also, in the more preferred embodiments, be conducted in the absence of any solvents. When carrying out these preferred embodiments of the invention, the solubility of the blocked ("reactivity modified") polyamine composition (and all ingredients therein) in the isocyanate substrate composition must be allowed for, since otherwise a separation will likely occur. The process may, if desired, be conducted using inert (aprotic) solvents of the types described hereinabove. This is particularly useful when the compatability between the blocked polyamine composition and the isocyanate substrate composition is poor. The solvents may be used to dilute either the blocked polyamine composition, the isocyanate substrate composition, or both. Examples of specific solvents which are suitable include benzene, toluene, chlorobenzene, o-dichlorobenzene, butyl acetate, ethylene glycol monomethyl ether acetate, methyl ethyl ketone, chloroform, methylene chloride, and the like.

According to the preferred (solvent free) embodiments, the blocked polyamine composition and the isocyanate substrate composition are combined and mixed, in appropriate amounts, in a chemical reactor at a temperature and pressure which is sufficient to promote the desired formation of the urea and/or biuret modified isocyanate composition. The reacting mixture may be agitated until the reaction has reached the desired state of completion. According to the most preferred embodiments, the "chemical reactor" is simply a static (in-line) mixer or an impingement mixing apparatus into which the reagent streams are fed at a rate, temperature, pressure, and weight ratio which is most appropriate for preparing the modified isocyanate compositions. Under this, most preferred, processing arrangement, the need for bulky processing equipment and for lengthy synthetic operations is largely eliminated.

In most cases it is possible, and preferable, to prepare the modified isocyanate compositions at temperatures between 20° and 50° C. and at mixing pressures of between 1 and 10 Atm. It is not generally necessary to perform this reaction at temperatures higher than about 100° C. and/or mixing pressures greater than about 100 Atm. There may be instances, however, wherein temperatures as high as 200° C. and/or mixing pressures up to 1000 Atm are called for during a portion of the reaction, or during the entire reaction.

The more severe processing conditions are likely to be required when working with blocked polyamine compositions and/or isocyanate substrate compositions which are highly reactive, for example, when the agent used to block the polyamines is very labile (as in the case of carbamic acid complexes, formed from $CO_2$ and the polyamines), when a weak blocking agent is used (as in the case of the ammonium carboxylate or ammonium carbonate salts of the polyamines), when the equivalent weight of the polyamine composition itself is very low (i.e., less than about 200), when the polyamine contains ingredients of low equivalent weight, when the number amine functionality of the polyamine composition itself or any ingredient therein is very high (i.e., higher than about 6), and/or when any or all of the aforementioned conditions exists during the urea and/or biuret modification of an isocyanate substrate composition which consists of or contains aromatic isocyanates having number averaged isocyanate functionalities of much higher than about 2.

The number averaged isocyanate (NCO) and or isothiocyanate (NCS) functionality of any mixture of X isocyanate and/or isothiocyanate containing ingredients is given by Formula II below. Henceforth the term "isocyanate" will be used to donate speices containing organically bound isocyanate (NCO) and/or isothiocyanate (NCS) groups:

$$F_1 = \left( \sum_{J=1}^{J=X} \left[ \frac{F_J K_J}{MW_J} \right] \right) \bigg/ \left( \sum_{J=1}^{J=X} \left[ \frac{K_J}{MW_J} \right] \right)$$

wherein
$F_I$=Number averaged isocyanate functionality of the composition.
X=Number of distinct molecular species in the composition which contain isocyanate groups.
$K_J$=The weight of the Jth molecular component in the composition which contains isocyanate groups.
$F_J$=The number of isocyanate groups in the Jth component of the composition which contains isocyanate groups.
$MW_J$=The molecular weight of the Jth component of the composition, which contains isocyanate groups.

Great care must be taken to insure that the speed and quality of the mixing between the blocked polyamine composition and the isocyanate substrate composition is adequate, and that these key ingredients are accurately and continuously metered into the reactor. This is to insure that unfavorable concentration ratios do not develop at any point in the reactor, or at any time during the process. Such unfavorable (or anisotropic) component ratios can result in the formation of insoluble gels and precipitates.

The amount of biuret formation (biuretization) which occurs during the synthesis of the urea and/or biuret modified isocyanate compositions of the instant invention can be influenced by the processing conditions used. Generally, the higher the reaction temperature, and the longer the residence time at a given temperature; the greater the extent of biuretization. The extent of biuretization has important implications for both the physical properties of polymeric compositions derived from the modified isocyanate compositions of the invention, and for the processing of said modified isocyanate compositions into useful polymeric end products. This is true because the extent of biuretization effects both the final number averaged isocyanate functionality of the modified compositions and the concentration of free isocyanate groups which remain, unreacted, in said compositions. These facts are illustrated in the following diagram:

Urea:

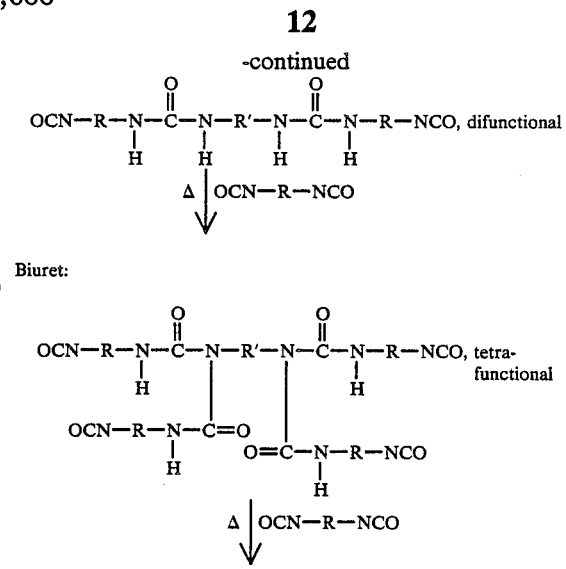

Higher Order Biuret and Polyuret Structures of Functionality greater than 4.

Of course, the level of functionality in the modified isocyanate composition is closely related to the density of crosslinks in polymeric compositions derived therefrom. A low level of functionality and hence a low level of biuretization, in the modified isocyanate compositions, is desirable when said compositions are destined for use in the synthesis of elastomeric or flexible materials such as flexible foams, sealants, soft coatings, molded elastomers, and the like. Such materials generally exhibit better toughness (i.e., better elongation, resistance to tearing, abrasion resistance, etc.) when they contain a low density of crosslinks. The use of low-functionality isocyanates is also advantageous from the viewpoint of processing. Low functionality generally means longer gel times, during the preparation of polymeric materials. Another important advantage of maintaining a low level of biuretization (low functionality) is improved homogeneity and stability in the resulting modified isocyanate compositions. Exhaustive biuretization can, in some instances, result in the formation of insoluble gels and, in extreme cases, in bulk gellation. Therefore, if biuretization is to be minimized, the mildest possible processing conditions, should be used during the reaction between the blocked polyamine compositions and the isocyanate substrate compositions.

When preparing modified isocyanate compositions, which are destined for use in synthesizing highly crosslinked polymeric materials: such as rigid foams, laquers, fabric treatments, and the like; a higher level of biuretization may be desired. In these circumstances, more severe processing conditions may be justified when conducting the reaction between the blocked polyamine compositions and isocyanate substrate compositions.

The reaction between the blocked polyamine compositions and the isocyanate substrates may be conducted according to a process which consists of several distinct steps, each performed under a different set of conditions (temperature, pressure, etc.) and each involving a different blend of reagents. In the most preferred cases, however, the urea and/or biuret modified compositions may be prepared according to a process which consists of a single step, under a single set of conditions. The precise choice of processing conditions will depend critically upon the type of blocked polyamine composition and upon the isocyanate substrate. In certain preferred embodiments, when the amine, equivalent weight of the polyamine is at least 100 preferable greater than about 250 and most preferably greater than 1000. When the polyamine consists largely of polymers or copolymers of propylene oxide and/or ethylene oxide, it is rarely necessary to exceed temperatures of 50° C., pressures of about 5 Atm, and reaction times of 0.25 hrs.

The urea and/or biuret modified isocyanate compositions of the invention may be prepared by using an excess of isocyanate groups (i.e., including any isothiocyanate groups) over active hydrogen groups of at least 1.5:1 on an equivalents basis. In the more preferred embodiments of the invention, however, the ratio of isocyanate groups to the sum total of active hydrogen groups used to prepare the modified isocyanate compositions of the invention is at least 3:1, on an equivalents basis. In the most preferred embodiments, the ratio of isocyanate groups to the sum total of active hydrogen groups used to prepare the modified isocyanate compositions of the invention is at least 5:1, on an equivalents basis. The "active hydrogen groups" referred to hereinabove are to be understood as the sum of the reactive (primary and secondary) amine groups present (whether free, or in "blocked" or latent form) within the blocked polyamine composition, and any additional Zerewitinoff active hydrogen groups, such as alcohols, phenols, thiols, carboxylic acids, and the like.

The extent of biuretization which occurs during the reaction of the blocked polyamine compositions with the isocyanate substrate compositions of this invention depends upon a large number of factors. These include the choice of isocyanates and blocked polyamines which are employed, the ratio of isocyanate equivalents to total active hydrogen equivalents used in the formulation, the processing conditions, the choice of blocking agent used, and the level of blocking agent used. As explained hereinabove, excessive biuretization may be disadvantageous in many cases (i.e., when a low level of functionality is desired in the resultant modified isocyanate composition). Some biuretization may be highly desirable in cases wherein a higher level of isocyanate functionality is needed. The importance of functionality notwithstanding a certain degree of biuretization is, in some kinds of modified isocyanate compositions, highly desirable from the viewpoint of improved product stability and appearance. Controlled amounts biuretization can reduce the tendency, for certain modified isocyanate compositions, to phase-separate into distinct isocyanate and polyurea layers. Therefore, the extent of biuretization which is desired in any particular modified isocyanate composition, as prepared within and according to the instant invention, and hence the processing conditions required, is determined by the physical properties of the modified isocyanate composition itself (for example, the rate of bulk separation—if any, as a function of the storage temperature: the viscosity as a function of temperature; the appearance of the composition), and by the physical properties of polymeric compositions which are derived from these modified isocyanate compositions. Sincetthe number of potential modified isocyanate compositions which may be prepared within the scope of the present invention and since the number of potential polymeric compositions which may be derived from any one of these isocyanate formulations are quite large, it is not possible to uniquely specify processing conditions which are optimal for all of them. It is to be understood that the property criteria by which any given modified isocyanate composition is to be judged will depend upon the intended end use application.

One of the purposes of this invention is to provide a highly versatile method for preparing modified isocyanate compositions, and a range of said compositions, in which the level of biuretization may advantageously be controlled. The extent of biuretization in these compositions may be monitored by chemical means such as by the titrimetric determination of residual isocyanate (or isothiocyanate) group concentrations; or by spectroscopic means, such as the comparison of the relative positions and intensities of absorbtions in the infrared spectra of the modified isocyanate compositions with homologous absorbtions in model compounds. The use of the monitoring techniques is illustrated within the attendant Examples. The successful application of these techniques will be readily apparent to those skilled in the art.

The modified isocyanate compositions herein disclosed are valuable for use in the preparations of polyurethane, polyurethaneurea, polyurea, and polyamide containing plastics materials by reaction with the appropriate active hydrogen compounds, under appropriate conditions.

Any suitable organic compound containing at least two active hydrogen containing groups as determined by the Zerewitinoff method, said groups being reactive with an isocyanate group, may be reacted with an organic polyisocyanate prepared in accordance with the process of the present invention. The active hydrogen atoms are usually attached to oxygen, nitrogen or sulphur atoms. Thus, suitable active hydrogen containing groups as determined by the Zerewitinoff method which are reactive with an isocyanate group include —OH, —NH$_2$, —COOH, —SH and the like. Examples of suitable types of organic compounds containing at least two active hydrogen containing groups which are reactive with an isocyanate group are hydroxyl polyesters, polyacetals, polyhydric polyalkylene ethers, polyhydric polythioethers, aliphatic polyols, including alkane, alkene and alkyne diols, triols, tetrols and the like; aliphatic thiols including alkane, alkene and alkyne thiols having two or more —SH groups: polyamines including both aromatic, aliphatic and heterocyclic diamines, triamines, tetramines and the like: as well as mixtures thereof. Of course, compounds which contain two or more different groups within the above-defined classes may also be used in accordance with the process of the present invention such as, for example, amino alcohols which contain an amino group and an hydroxyl group, amino alcohols which contain two amino groups and one hydroxyl group and the like. Also, compounds which contain one —SH group and one —OH group or two —OH groups and one —SH group as well as those which contain an amino group and an —SH group and the like may be used.

The molecular weight of the organic compounds containing these active hydrogen containing groups is not critical. It is preferable, however, that at least one of the organic compounds, containing at least two active hydrogen containing groups which is used in production of plastic materials, has a molecular weight of at least 200 and preferably between 500 and about 5,000 with preferably between two and six active hydrogen containing groups per molecule. A satisfactory upper limit for the molecular weight of the organic compound containing at least two active hydrogen containing groups is about 10,000 but this limitation is not critical so long as satisfactory mixing of the organic compound, containing at least two active hydrogen containing groups, with the polyisocyanate composition can be obtained. In addition to the high molecular weight organic compound containing at least two active hydrogen containing groups, it is desirable to use an organic compound of this type having a molecular weight below about 750 and preferably below about 500.

Any suitable amino functional polyether resin, such as the types described hereinabove, may be used in the preparation of plastics materials from the modified isocyanate compositions of the instant invention. It is also suitable to use active hydrogen compounds which are substantially or entirely free of amine functionality when preparing plastics materials from the modified isocyanate compositions disclosed herein.

Any suitable hydroxyl containing polyester may be used such as are obtained, for example, from polycarboxylic acids and polyhydric alcohols. Any suitable polycarboxylic acid may be used such as, for example, oxalic acid, malonic acid, succinic acid, glutaric acid, adipic acid, pimelic acid, suberic acid, azelaic acid, sebacic acid, brassylic acid, thapsic acid, maleic acid, fumaric acid, glutaconic acid, alpha-hydromuconic acid, beta-hydromuconic acid, alpha-butyl-alpha-ethyl-glutaric acid, alpha, beta-diethylsuccinic acid, trimellitic acid, mellophanic acid, prehnitic acid, isophthalic acid, terephthalic acid, hemimellitic acid, benzenepentacarboxylic acid, 1,4-cyclohexanedicarboxylic acid, 3,4,9,10-perylenetetracarboxylic acid and the like. Any suitable polyhydric alcohol may be used such as, for example, ethylene glycol, 1,3-propylene glycol, 1,2-propylene glycol, 1,4-butylene glycol, 1,3butylene glycol, 1,2-butylene glycol, 1,5-pentane diol, 1,4-pentane diol: 1,3-pentane diol, 1,6-hexane diol, 1,7-heptane diol, glycerine, trimethylol propane, 1,3,6hexane triol, triethanolamine, pentaerythritol, sorbitol and the like.

Any suitable polyhydric polyalkylene ether may be used such as, for example, the condensation product of an alkylene oxide or of an alkylene oxide with a polyhydric alcohol. Any suitable polyhydric alcohol may be used such as those disclosed above for use in the preparation of the hydroxyl polyesters. Any suitable alkylene oxide may be used such as, for example, ethylene oxide, propylene oxide, butylene oxide, amylene oxide and the like. Of course, the polyhydric polyalkylene ethers can be prepared from other starting materials such as, for example, tetrahydrofuran, epihalohydrins such as, for example, epichlorohydrin and the like as well as aralkylene oxides such as, for example, styrene oxide and the like. The polyhydric polyalkylene ethers may have either primary or secondary hydroxyl groups and preferably are polyhydric polyalkylene ethers prepared from alkylene oxides having from two to five carbon atoms such as, for example, polyethylene ether glycols, polypropylene ether glycols, polybutylene ether glycols and the like. It is often advantageous to employ some trihydric or higher polyhydrdic alcohol such as glycerine, trimethylol propane, pentaerythritol and the like in the preparation of the polyhydric polyalkylene ethers so that some branching exists in the product. Generally speaking, it is advantageous to condense from about 5 to about 30 mols of alkylene oxide per functional group of the trihydric or higher polyhydric alcohol. The polyhydric polyalkylene ethers may be prepared by any known process such as, for example, the process disclosed by Wurtz in 1859 and in Encyclopedia of Chemical Technology, vol. 7, pp. 257–262, published by Interscience Publishers, Inc. (1951), or in U.S. Pat. No. 1,922,459.

Any suitable polyhydric polythioether may be used such as, for example, the condensation product of thiodiglycol or the reaction product of a polyhydric alcohol such as is disclosed above for the preparation of the hydroxyl polyesters with any other suitable thioether glycol. Other suitable polyhydric polythioethers are disclosed in U.S. Pat. Nos. 2,862,972 and 2,900,368.

The hydroxyl polyester may also be a polyester amide such as is obtained, for example, by including some amino alcohol or amine in the reactants for the preparation of the polyesters. Thus, polyester amides may be obtained by condensing an amino alcohol such as ethanolamine with the polycarboxylic acids set forth above or they may be made using the same components that make up the hydroxyl polyester with only a portion of the components being a diamine such as ethylene diamine and the like.

Any suitable polyacetal may be used, such as, for example, the reaction product of formaldehyde or other suitable aldehyde with a polyhydric alcohol such as those disclosed above for use in the preparation of the hydroxyl polyester.

Any suitable aliphatic polyol may be used such as, for example, alkane diols such as, for example, ethylene glycol, 1,3-propylene glycol, 1,2-propylene glycol, 1,4-butylene glycol, 1,3-butylene glycol, 1,5-pentanediol-1,4-butane diol, 1,3-pentane diol, 1,6-hexane diol, 1,7heptane diol, 2,2-dimethyl-1,3-propane diol, 1,8-octane diol and the like including 1,20-eicosane diol and the like: alkene diols such as, for example, 2-butene-1,4-diol, 2-pentene-1,5-diol, 2-hexene-1,6-diol, 2-heptene-1,7-diol and the like: alkyne diols such as, for example, 2-butyne1,4-diol, and the like; alkane triols such as, for example, 1,3,6-hexanetriol, 1,3,7-heptane triol, 1,4,8-octane triols, 1,6,12-dodecane triol and the like; alkene triols such as, 1-hexene-3,4,6-triol and the like; alkane tetrols such as, for example, 1,2,5,6-hexane tetrol and the like; alkyne tetrols such as for example, 4-octyne-1,2,7,8-tetrol and the like; alkene tetrols such as, for example, 3-heptene-1,2,6,7-tetrol and the like.

Any suitable aliphatic thiol incuding alkane thiols containing two or more —SH groups may be used such as, for example, 1,2-ethane dithiol, 1,2-propane dithiol, 1,3-propane dithiol, 1,6-hexane dithiol, 1,3,6-hexane trithiol and the like; alkene thiols such as, for example, 2-butene-1,4-dithiol and the like; alkyne thiols such as, for example, 3-hexyne-1,6-dithiol and the like.

Any suitable polyamine may be used for example, aromatic polyamines such as, for example, p-amino aniline, 1,5-diamino naphthalene, 2,4-diamino toluylene, 1,3,5-benzene benzene triamine, 1,2,3-benzene triamine, 1,4,5,8-naphthalene tetramine and the like; aliphatic polyamines such as, for example, ethylene diamine, 1,3-propylene diamine, 1,4-butylene diamine, 1,3-butylene diamine, diethylene triamine, triethylene tetramine, 1,3,6-hexane triamine, 1,3,5,7-heptane tetramine and the like: heterocyclic polyamines such as, for example, 2,6-diamino pyridine, 2,4-diamino-5-aminomethyl pyrimidine, 2,5-diamino-1,3,4-thiadiazol and the like.

Other alcohol compounds which do not necessarily fit within any of the previously set forth classes of compounds and which nevertheless contain active hydrogen containing groups which are quite suitable for the production of the polyurethane plastics of the present invention are pentaerythritol, sorbitol, triethanolamine, mannitol, N,N,N',N'-tetrakis(2-hydroxy propyl)ethylene diamine, as well as compounds of any of the classes set forth which are substituted with halogen such as, for example, chloro, iodo, bromo and the like; nitro; alkoxy, such as, for example, methoxy, ethoxy, propoxy, butoxy, and the like; carboalkoxy such as, for example, carbomethoxy, carbethoxy and the like; dialkyl amino such as, for example, dimethyl amino, diethyl amino, dipropyl amino, methylethyl amino and the like; mercapto, carbonyl, thiocarbonyl, phosphoryl, phosphate and the like.

It is also possible to use polyphosphites or alkoxylated phosphoric acids such as, for example, those disclosed in U.S. Pat. Nos. 3,009,939 and 3,061,625.

The polyisocyanates of the invention are useful for the preparation of cellular polyurethane plastics by reaction thereof with an active hydrogen containing compound in the presence of a blowing agent. Suitable processes for the preparation of cellular polyurethane plastics are disclosed in U.S. Re. Pat. No. 24,514 together with suitable machinery to be used in conjunction therewith. When water is added as the blowing agent, corresponding quantities of excess isocyanate to react with the water and produce carbon dioxide may be used. It is also possible to proceed with the preparation of the polyurethane plastics by a prepolymer technique wherein an excess of organic polyisocyanate is reacted in a first step with the polyol of the present invention to prepare a prepolymer having free —NCO groups which is then reacted in a second step with water to prepare a foam. Alternately, the components may be reacted in a single working step. Furthermore, instead of water, low boiling hydrocarbons such as pentane, hexane, heptane, pentene and the like; azo compounds, halogenated hydrocarbons such as, dichloro, difluoromethane, trichlorofluoromethane, dichlorodifluoroethane, vinylidene chloride and the like may be used as blowing agents. It is often advantageous in the production of cellular polyurethane plastics to include other additives in the reaction mixture such as, for example, emulsifiers, foam stabilizers, coloring agents, fillers and the like. It is particularly advantageous to employ an emulsifier such as, for example, sulphonated castor oil and/or a foam stabilizer such as a silicone oil such as, for example, a polydimethyl siloxane or an alkyl silane polyoxy alkylene block copolymer. The latter type of silicone oil is disclosed in U.S. Pat. No. 2,834,748. Where polyhydric polyalkylene ethers are included in the reaction mixture to prepare a cellular polyurethane plastic, it is preferred to employ a silicone oil of the above patent within the scope of the formula

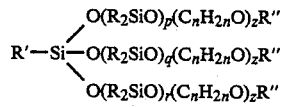

wherein R, R' and R" are alkyl radicals having 1 to 4 carbon atoms; p, q and r each have a value of from 4 to 8 and $(C_nH_{2n}O)_z$ is a mixed polyoxyethylene oxypropylene group containing from 15 to 19 oxyethylene units and from 11 to 15 oxypropylene units with a z equal to from about 26 to about 34. Most preferred is a compound having the formula

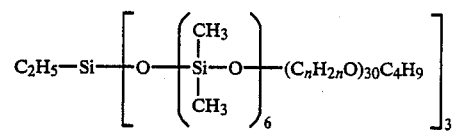

wherein $(C_nH_{2n}O)$ is a mixed polyoxyethylene and oxypropylene block copolymer containing about 17 oxyethylene units and about 13 oxypropylene units.

Suitable catalysts may be used to speed up the reaction if desired such as, for example, dimethyl benzylamine, dimethylstearyl amine, permethylated diethylene triamine, N-methyl-N'-dimethylaminoethyl piperazine, N, N'-endoethylene piperazine, N-alkyl morpholines; tertiary aminoethers such as, for example, 1-alkoxy-3-dialkylaminopropane, tertiary amines with ester groups, salts of tertiary amines, especially with organic acids such as, for example, oleic acid, benzoic acid, and the like, dibutyl tin dilaurate, dibutyl tin di-2-ethyl hexoate, dibutyl-tin-bis-(dimethylamino caproate), stannous octoate, lead naphthenate, ferric actylacetonate, mixtures thereof and any other catalyst which will promote the reaction between isocyanate groups and active hydrogen atoms as determined by the Zerewitinoff method as those disclosed in "Catalysis of the Isocyanate-Hydroxyl Reaction," J. W. Britain and P. G. Gemeinhardt, Journal of Applied Polymer Science, vol. IV, Issue No. 11, pp. 207–211 (1960).

The polyisocyanates of the invention may also be used for the production of coating compositions. In this case, the organic compound containing active hydrogen containing groups is reacted with the polyisocyanates of the invention in an inert organic solvent for example, methyl formamide, the diethyl ether of diethylene glycol, benzene, xylene, benzine and the like.

It is also possible to use the polyisocyanates of the invention in the preparation of elastomeric products which are nonporous for example by reacting an organic compound containing active hydrogen containing groups with an excess of the polyisocyanate of the invention, in a first step, to prepare an isocyanato-terminated prepolymer under anhydrous conditions. This prepolymer may then be reacted, in a second step, with a chain extending agent such as an organic low molecular weight diol or diamine, and casting the resulting mixture in a mold.

The modified isocyanate compositions of the invention are particularly useful in the preparation plastics materials via the reaction invention molding (RIM) process, in which the isocyanate composition is rapidly mixed with one or more active hydrogen containing species and the resulting mixture is allowed to react and cure within a closed mold. In the most preferred embodiments of the process, the active hydrogen containing species consists of a mixture of one or more high molecular weight active hydrogen compounds, with molecular weights greater than about 1500, and one or more chain extending agents, having molecular weights less than about 500. Suitable types of active hydrogen containing species are as defined hereinabove. Chain extending agents which are particularly preferred include ethylene glycol; 1,4-butanediol; $H_2O$; hydroquinone di(beta-hydroxyethyl)ether; 4,4'- and 2,4'-diphenylmethanediamines; 2,4- and 2,6-toluenediamines; 1-methyl-3,5-diethyl-2,4-diaminobenzene, 1-methyl-3,5-diethyl-2,6-diaminobenzene (both of these materials are also called diethyltoluene diamine or DETDA), 1,3,5-triethyl-2,6-diaminobenzene, 3,5,3',5'-tetraethyl-4,4''-diaminodiphenylmethane and the like. Particularly preferred aromatic diamine chain extenders are 1-methyl-3,5-diethyl-2,4-diaminobenzene or a mixture of this compound with 1-methyl-3,5-diethyl-2,6-diaminobenzene. As described in U.S. Pat. Nos. 4,218,543; 4,246,363; and 4,269,945 which are hereby incorporated by reference.

Other chain extenders which find use in the method are low molecular weight polyoxyalkylene polyamines which contain terminal amine groups and are represented by the formula

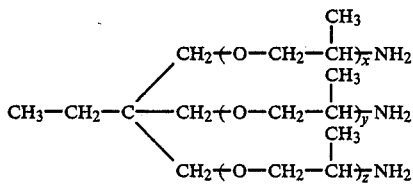

wherein x+y+z has a value of about 5.3. The average amine hydrogen equivalent weight is about 67 and the product is commercially available from Texaco Chemical Company as JEFFAMINE ® T-403. Another related polyoxypropylene polyamine is represented by the formula

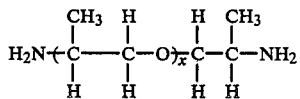

wherein x has a value of about 5.6. This product has an average amine hydrogen equivalent weight of about 100 and is commercially available from Texaco Chemical Company as JEFFAMINE D-400. The product having the same formula as above wherein x has an average value of about 2.6 is also useful. This product has an average amine hydrogen equivalent weight of about 57.5 and is commercially available from Texaco Chemical Company as JEFFAMINE D-230.

Other chain extenders will be apparent to those skilled in the art and the above recitation is not intended to be a limitation on the invention claimed herein.

The modified isocyanate compositions of the instant invention may be useful as isocyanate components in the synthesis of polyurea elastomers and plastics via the RIM process. These polyurea formulations are generally either substantially or entirely free of urethane linkages. These RIM polyurea compositions are prepared via the reaction of isocyanate(s) with amine terminated polyether resins and amino functional chain extending agents, as described in U.S. Pat. Nos. 4,420,570; 4,448,904; 4,474,900; 4,474,901; and European patent application EP-No. 92,672 A2; and EP-No. 93,862 A1; which are incorporated herein by reference.

The plastics compositions which may be prepared from the modified isocyanate compositions of the invention are useful, for example; in the form of flexible and semiflexible foams for furniture and automotive cushions, carpet backings, sound and impact absorbing wall coverings; in the form of elastomeric facias for automobiles; molded industrial elastomers such as belts and gear wheels; in the form of molded structural components such as automobile body panels and such as housings for business machines; in the form of coatings for wood, metals, glass, and fabrics; in the form of rigid plastics and foams thereof; in structural laminates and composites; and in numerous other forms which are adapted to specific applications and which will be familiar to those skilled in the art.

The invention is further illustrated by the following examples. These examples are presented for purpose of illustration and are not intended to be construed as limiting the scope of the invention.

Glossary of Terms

Polyamine A: A linear 2000 molecular weight primary amine terminated polyoxypropylene diamine, which is commercially available from Texaco Chemical Corp. "Jeffamine D-2000."

Polyamine B: A linear 400 molecular weight primary amine terminated polyoxypropylene diamine, which is commercially available from Texaco Chemical Corp. as "Jeffamine D-400."

Polyamine C: A linear 4000 molecular weight Primary amine terminated polyoxypropylene diamine, which is commercially available from Texaco Chemical Corp. as "Jeffamine D-4000."

Polyamine D: A glycerol initiated 5000 molecular weight primary amine terminated polyoxypropylene triamine, which is commercially available from Texaco Chemical Corp. as "Jeffamine T-5000."

Polyamine E: A glyceral initiated 3000 molecular weight primary amine terminated polyoxypropylene triamine, which is commerically available from Texaco Chemical Corp. as Jeffamine T-3000.

Polyamine F: A linear 2000 molecular weight polyoxyethylene polyoxypropylene copolymer based diprimary diamine in which about 94 mole percent of the total oxyalkylene units in the chain are oxyethylene units and the remaining 8 mole percent are oxypropylene units. This substance is commercially available from Texaco Chemical Co. as "Jeffamine ED-2001."

Polyamine G: A linear 600 molecular weight primary amine terminated polyoxyethylene polyoxypropylene copolymer diamine in which about 77 mole percent of the total oxyalkylene units in the chain are oxyethylene units and the remaining 23 mole percent are oxypropylene units. This substance is commercially available from Texaco Chemical Co. as "Jeffamine ED-600."

Polyamine H: An 80:20 mixture, by weight, of 3,5-diethyl-Z,4-diaminotoluene and 3,5-diethyl-2,6-diaminotoluene. A commercially available mixture of aromatic diprimary diamines, as obtained from Ethyl Corporation.

Isocyanate I: Pure 4,4'-diphenylmethane diisocyanate, containing not more than 2% by weight of the 2,4'-diphenylmethane diisocyanate isomer. This material is commercially available from Rubicon Chemicals Inc.

Isocyanate J: A mixture consisting of approximately 80% by weight of 4,4'-diphenylmethane diisocyanate and about 20% by weight 2,4'-diphenylmethane diisocyanate. Commercially available from Rubicon Chemicals Inc.

Isocyanate K: A uretonimine modified derivative of Isocyanate I, having a free isocyanate (NCO) content of 29.3% by weight and a number averaged functionality of about 2.15. This substance is commercially available from Rubicon Chemicals Inc., as "Rubinate LF-168."

Isocyanate L: A uretonimine modified derivative of isocyanate J, having a free isocyanate (NCO) content of 31.0% by weight and a number averaged functionality of about 2.08. This substance is available from Rubicon Chemicals Inc. as "Rubinate Xl-208."

Isocyanate M: Phenyl isocyanate.

Isocyanate N: A urethane pseudoprepolymer modified derivative of Isocyanate I which is prepared by reacting Isocyanate I with a mixture of low molecular weight glycols. This substance has a free isocyanate (NCO) content of about 23.0% by weight, a number averaged functionality of 2.00, and is commercially available from Rubicon Chemicals Inc. as "Rubinate LF-179."

Isocyanate O: A blend consisting of 50% by weight Isocyanate K and 50% by weight Isocyanate N. This substance is commercially available from Rubicon Chemicals Inc. as "Rubinate LF-167."

Isocyanate P: A mixture consisting of about 70% by weight 4,4'-diphenylmethane diisocyanate and about 30% 2,4'-diphenylmethane diisocyanate.

Isocyanate Q: A mixture consisting of about 80% 2,4-toluene diisocyanate and about 20% 2,6-toluene diisocyanate. This substance is commercially available from Rubicon Chemicals Inc. as "Rubinate TDI."

Isocyanate R: Is the meta isomer of tetramethylxylene diisocyanate. This material is commercially available from American Cyanamide Corp. as "m-TMXDI."

Isocyanate S: Polymeric polyphenylmethane polyisocyanate, or "crude MDI." A mixture of various isomers of diphenylmethane diisocyanate with a series of higher functionality methylene bridged polyphenylmethane isocyanates, in a ratio of about 1:1 by weight. This substance has a number averaged isocyanate functionality of about 2.75 and a functional group (NCO) concentration of about 31.5% by weight. It is commerically available from Rubicon Chemicals Inc. as "Rubinate M."

Isocyanate T: A modified version of Isocyanate S, in which the diphenylmethane diisocyanate isomer content has been increased, by blending with Isocyanate J. This substance has a number averaged isocyanate functionality of about 2.40 and a functional group (NCO) concentration of about 31.5% by weight. It is commercially available from Rubicon Chemicals Inc. as "Rubinate XI-182."

Examples 1-10 are intended to illustrate convenient methods for preparing the blocked, "retarded," or "reactivity modified" polyamine compositions which are useful in the practice of the instant invention:

EXAMPLE 1

A flask was charged with 350 g of Polyamine D. The flask, equipped with a thermometer, overhead stirrer, and an inert gas inlet, was gently and continuously purged with a stream of dry nitrogen. A gas sparging tube was inserted into the flask, with the outlet well below the level of the liquid (Polyamine D). The liquid was gently agitated and sparged, beneath its surface, with anhydrous hydrochloric acid (HCl) in large excess. The excess HCl was swept out of the flask via the nitrogen purge. The HCl sparging was initiated at ambient temperatures (20°-25° C.) and continued until after the reaction exotherm had peaked and subsided. The total reaction time was 1 hr. (HCl sparging) and the peak exotherm reached 53° C. during this preparation. The product was a clear liquid.

EXAMPLE 2

Following a procedure analogous to that described in Example 1, a 350 g sample of the anhydrous hydrochloride salt of Polyamine E was prepared. The total sparging time was approximately 1 hr. The product was a clear liquid.

EXAMPLE 3

Following a procedure analogous to that described in Example 1, a 350 g sample of the anhydrous hydrochloride salt of Polyamine G was prepared. The total sparging time was approximately 1 hr. The product was a clear liquid.

EXAMPLE 4

Following a procedure analogous to that described in Example 1, a 350 g sample of the anhydrous hydrochloride salt of Polyamine C was prepared. The total sparging time was approximately 1 hr. The product was a clear liquid.

EXAMPLE 5

A flask, equiped with thermometer, overhead stirrer, and a purge of dry nitrogen, was charged with 300 g of Polyamine C. Adipic acid, 11.0 g, was then suspended in the liquid polyamine. The resulting suspension was agitated and heated until all the solids dissolved. The system became clear and homogeneous at 85° C. The product remained homogeneous at ambient temperatures.

EXAMPLE 6

Following a procedure analogous to that described in Example 5, a 300 g sample of Polyamine D was modified with 13.16 g of adipic acid. The adipic acid was initially suspended in the polyamine. The system was then heated until clear (85° C.). The product was a clear homogeneous liquid at ambient temperatures.

EXAMPLE 7

A flask was charged with 325 g of Polyamine C. The flask, equipped with a thermometer, overhead stirrer, and an inert gas inlet, was gently and continuously purged with a stream of dry nitrogen. A gas purging tube was inserted into the flask, with the outlet well below the level of the liquid (Polyamine C). The liquid was gently agitated and sparged, beneath its surface, with anhydrous carbon dioxide ($CO_2$) in large excess. The excess $CO_2$ was swept out of the flask via the nitrogen purge. The $CO_2$ sparging was initiated at 23° C. and continued until after the reaction exotherm had peaked and subsided. The total reaction time was 1 hr. ($CO_2$ sparging) and the peak exotherm reached 30° C. during this preparation. The product was a clear liquid.

EXAMPLE 8

Following a procedure analogous to that described in Example 7, a 325 g sample of the carbon dioxide modified derivative of Polyamine A was prepared. The total sparging time was appoximately 1 hr. and the peak exotherm reached 34° C. The product was a clear liquid.

EXAMPLE 9

A flask was charged with 283.2 g of Polyamine D. The flask, equipped with a thermometer, an overhead stirrer, and an inert gas inlet, was maintained under a slight positive pressure with dry nitrogen. The liquid Polyamine D was agitated and trimethylsilylnitrile, 16.85 g, was added steadily via syringe over a period of 2 min. The temperature of the reaction increased from 23° C. to 31° C. during the addition—due to a spontaneous exotherm. Modest gas evolution was noted. This gas was allowed to expand against the nitrogen back pressure and escape through a side outlet in the nitrogen line. The gas was vented into a fume hood. After the addition was completed, the temperature of the reaction was increased to 80° C. over 13 min. and maintained at 80° C., with continued agitation, for an additional 40 min. The flask was then attached to a vacuum line and the pressure over the liquid mixture was reduced from ambient to approximately 1 mm. Hg. Vigorous gas evolution was noted during this depressurization step. This gas was condenced in a dry ice trap. The outlet from the vacuum pump was vented intoa fume hood. Gas evolution was observed to have ceased 8 min. after the vacuum was applied. The temperature of the system was further increased to 105° C. over a period 10 min. Heating was then discontinued and the product was allowed to cool. Agitation was discontinued and the pressure in the flask was allowed to increase, to ambient, by introduction of dry nitrogen. The product was a clear liquid.

EXAMPLE 10

Following a procedure closely analogous to that used in Example 9, a sample consisting of 100 g of Polyamine B was reacted with 49 g of trimethylsilylnitrile. The total reaction time was 83 min., the maximum temperature reached during the vacuum degassing stage was 100° C., and the final product was a clear liquid.

EXAMPLE 11

A sample of the polyamine derivative prepared in Example 2 was added directly to a 90:10 (w/w) blend of Isocyanates J and K. The addition was performed at a temperature of 46° C. under an atmosphere of dry nitrogen. The isocyanate blend was agitated gently throughout the addition. The addition was conducted over a period of 43 min. Following the addition, the pressure within the reaction vessel was reduced to approximately 1 mm. Hg. and agitation was continued for 1 hr. longer. Pressure within the vessel was then increased to ambient, by slow introduction of dry nitrogen. Agitation was discontinued and the sample was stored, under an atmosphere of dry nitrogen, at ambient temperatures. The product was observed to be a clear homogeneous liquid. The product was free of solids, gels, or cloudiness after 3 weeks of storage. No solids or gels were observed at any point during the preparation. The final formulation is listed below, with each ingredient as a percent by weight of the total:
Isocyanate J=45.0%
Isocyanate K=5.0%
Derivative of Polyamine E (from Example 2)=50.0%

Attempts to form a composition analogous to that shown under Example 11, according to a procedure analogous to that described in Example 11, but using untreated Polyamine E (instead of the derivative prepared in Example 2) were not successful. Solids began forming instantly when Polyamine E was added to the isocyanate blend of Example 11. Continued addition of Polyamine E resulted in a steady buildup of gel-like solids.

EXAMPLE 12

A sample of the polyamine derivative prepared in Example 1 was added directly to a 90:10 (w/w) blend of Isocyanate J and K. The addition was performed at a temperature of 48° C. under an atmosphere of dry nitrogen. The isocyanate blend was agitated gently throughout the addition. The addition was conducted over a period of 26 min. Following the addition, the pressure within the reaction vessel was reduced to approximately 1 mm. Hg. and agitation was continued for 1 hr. longer. Pressure within the vessel was then increased to ambient, by slow introduction of dry nitrogen. Agitation was discontinued and the sample was stored, under an atmosphere of dry nitrogen, at ambient temperatures. The product was observed to be a clear homogeneous liquid. The product was free of solids, gels, or cloudiness after 6 weeks of storage. No solids or gels were observed at any point during the preparation. The final formulation is listed below, with each ingredient as a percent by weight of the total:
Isocyanate J=45.0%
Isocyanate K=5.0%
Derivative of Polyamine D (from Example 1)=50.0%

Attempts to form a composition analogous to that shown under Example 12, according to a procedure analogous to that described in Example 12, but using untreated Polyamine D (instead of the derivative prepared in Example 1), were not successful. Solids began forming instantly when Polyamine D was added to the isocyanate blend of Example 12. Continued addition of Polyamine D resulted in a steady buildup of gel-like solids.

EXAMPLE 13

A sample of the polyamine derivative of Example 3 was added directly to a sample of Isocyanate L. The procedure followed was closely analogous to that used in Examples 11 and 12, except that the addition time was 15 min. and the vacuum treatment of the crude product was omitted. The maximum temperature reached during the processing was 50° C. A sample of the product was transferred to a dry glass jar and allowed to cool, at ambient temperature, for 1 hr. under an atmosphere of dry nitrogen. The product was a clear liquid which was free of solids or gels. The final formulation is listed below, with each ingredient as a percent by weight of the total:
Isocyanate L=95.0%
Derivative of Polyamine G (from Example 3)=5.0%

Attempts to form a composition analogous to that shown under Example 13, according to a procedure analogous to that described in Example 13, but using untreated Polyamine G (instead of the derivative prepared in Example 3), were not successful. Solids began forming rapidly when Polyamine G was added to Isocyanate L. Continued addition resulted in a steady buildup of gel-like solids. These solids would not re-dissolve, even when the temperature of the heterogeneous mixture was increased to 80° C.

EXAMPLE 14

A sample of the polyamine derivative of Example 2 was added directly to a sample of Isocyanate S. The isocyanate was agitated gently during the addition and the reaction vessel was purged continuously with dry nitrogen. The addition was conducted over less than 2 min. at an initial temperature of 22° C. The temperature of the system increased to 42° C., due to the exotherm of the reaction. No solids or gels were observed during or after the addition, but the viscosity of the formulation increased to the point where further agitation became labored. The formulation is listed below, with each ingredient as a percent by weight:

Isocyanate S=50.0%
Derivative of Polyamine E (from Example 2)=50.0%

In order to reduce the viscosity of the modified isocyanate composition to manageable levels, the above formulation was back blended with Isocyanate S and the temperature of the initial blend was increased momentarily to 55° C. in order to facilitate mixing. The final formulation is listed below with each ingredient as a percent by weight:

Isocyanate S=75.0%
Derivative of Polyamine E (from Example 2)=25.0%

This final product was transferred to a dry glass jar and stored at ambient temperatures under an atmosphere of dry nitrogen. The product was observed to be a clear homogeneous liquid, free of solids or gels, after 7 days of storage. No solids, gels, or other signs of inhomogenity were observed at any point during the preparation or storage of this product.

Attempts to form a composition analogous to that shown under Example 14, according to a procedure analogous to that described in Example 14, but using untreated Polyamine E (instead of the derivative prepared in Example 2), were not successful. Solids began forming when the first drop of Polyamine E was added to Isocyanate S. Continued addition of Polyamine E resulted in a steady buildup of gel-like solids.

EXAMPLE 15

A sample of the polyamine derivative prepared in Example 10 was added directly to Isocyanate L. The isocyanate was agitated during the addition and the reaction vessel was purged continuously with a stream of dry nitrogen. The addition was conducted over 0.5 hrs. at a temperature of 50° C. The formulation thus prepared is listed below, with each ingredient as a percent by weight:

Isocyanate L=75.0%
Derivative of Polyamine B (from Example 10)=25.0%

This product, although homogeneous in bulk, was highly viscous at ambient temperatures. A sample of the product was reheated to 47° C. and back blended with Isocyanate L, with gentle agitation, to give the final formulation listed below:

Isocyanate L=85.0%
Derivative of Polyamine B (from Example 10)=15.0%

This final product was transferred to a dry glass jar and stored at ambinet temperatures under an atmosphere of dry nitrogen. The product was observed to be a clear pourable liquid and remained homogeneous in bulk after 1 month of storage.

Attempts to form a composition analogous to that shown under Example 15, according to a procedure analogous to that described in Example 15, but using untreated Polyamine B (instead of the derivative prepared in Example 10), were not successful. Solids began forming when the first drop of Polyamine B was introduced to Isocyanate L continued addition of Polyamine B resulted in a steady buildup of gel-like solids. These solids would not redissolve when the temperature of the reaction was increased to 80° C.

EXAMPLE 16

A sample of the polyamine derivative prepared in Example 9 was added directly to a blend of Isocyanate J and K. The isocyanate blend was agitated continuously during the addition and the reaction vessel was purged with a stream of dry nitrogen. The addition was conducted over a period of 26 min. and at a temperature of 50° C. The formulation thus prepared is listed below, with each ingredient as a percent by weight:

Isocyanate J=45.0%
Isocyanate K=5.0%
Derivative of Polyamine D (from Example 9)=50.0%

This product was clear, liquid and free of solids or gels at the conclusion of this reaction.

EXAMPLE 17

A sample of the polyamine derivative prepared in Example 8 was rapidly poured into a well agitated sample of Isocyanate L. This addition took place over a period of not more than 5 sec. The reaction vessel, containing the isocyanate, was continuously purged with dry nitrogen during the addition and subsequent mixing. The addition was conducted with both components at ambient temperatures. The formulation, thus prepared, is listed below with each ingredient as a percent by weight:

Isocyanate L=75.0%
Derivative of Polyamine A (from Example 8)=25.0%

Within about 5 sec. of the addition, vigorous foaming was observed. The system foamed to more than twice its original volume. This foaming rapdly subsided, and there remained a homogeneous liquid product. The reaction was accompanied by a mild exotherm. The maximum temperature reached during this experiment was 33° C. The product was allowed to cool, with gentle agitation, for 10 min. and was then transferred to a dry glass jar and sealed under an atmosphere of dry nitrogen. After approximately 12 hrs. storage at ambient temperatures, the product was found to have a viscosity of 975 cps (at 23° C.). The product was a clear homogeneous liquid, free of solids or gels. No solids, gels, or separations were observed at any point during the preparation of this product.

Attempts to form a composition analogous to that shown under Example 17, according to the procedure of Example 17, but using untreated Polyamine A (instead of the derivative prepared in Example 8), were not successful. Soft gelatinous semi-solids began forming during the addition of Polyamine A to Isocyanate L. At the conclusion of the reaction the product was clearly heterogeneous, with gelled solids evident. After approximately 12 hrs. storage at ambient temperatures, the product was found to have a viscosity of 3685 cps (at 23° C.). The product was opaque, heterogeneous, and showed evidence of bulk separation.

EXAMPLE 18

A bis-urea model compound was prepared by reacting Polyamine A with Isocyanate M, so as to provide 0.99 equivalents of isocyanate (NCO) per equivalent of amine ($NH_2$). The amine was, therefore, used in slight excess. The reaction was performed by mixing the ingredients, at ambient temperatures, under an atmosphere of dry nitrogen. The product of this reaction was a clear colorless liquid which exhibited a carbonyl stretch in the infrared spectrum at 1698 cm$^{-1}$.

A model biuret compound was prepared by reacting Polyamine A with Isocyanate M so as to provide 2.02 equivalents of isocyanate groups per equivalent of NH$_2$ or, in other words, 1.01 equivalents of "NCO" per equivalent of amine hydrogen. Thus a slight excess of isocyanate was used in the preparation. The reaction was performed by initially mixing the ingredients at ambient temperature, followed by heating at 120° C. for 75 min. and then 85° C. for 30 min. Under an atmosphere of dry nitrogen. The product was a clear pale yellow liquid which exhibited a principal carbonyl stretch in the infrared spectrum at 1721 cm$^{-1}$. This peak was notably absent in the spectrum of the model urea compound described hereinabove. Moreover, the starting polyamine and isocyanate used to prepare the model compounds are devoid of carbonyl species and, hence, devoid of carbonyl absorbtions in the infrared (the NCO group is, strictly speaking, an exception to this rule; but its absorbtion occurs above 2200 cm$^{-1}$ which places it well above the region of interest).

This particular pair of model compounds was selected because they contain key structural elements which are identical to those present in many of the modified isocyanate compositions which are compared in past examples. The structural elements are:

urea:

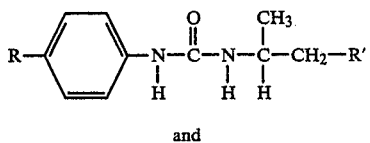

and

Biuret:

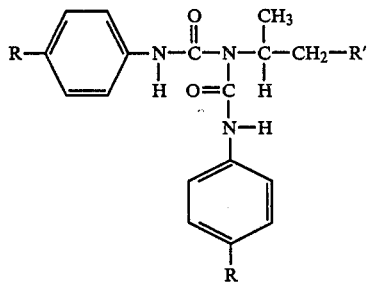

wherein R represents hydrogen or a —CH$_2$-terminated organic radical and R' represents a polyether chain. It is therefore possible to locate signals in the spectra of the modified polyisocyanate compositions which are homologous to those of the model compounds. In this way, the progress of the biuretization reaction can be followed as a function of processing conditions. The spectroscopic results can be compared to the concentration of residual isocyanate (NCO) groups in the sample. It is possible, also, to assess whether or not the blocked, or reactivity modified, polyamine composition has indeed reacted with the isocyanate substrate composition - to form urea and/or biuret linkages. The presence of carbonyl signals in the IR (below 2200 cm$^{-1}$) is generally diagnostic of reaction. Infrared analyses were performed on the modified isocyanate compositions prepared in Examples 11, 12, 14, 15, 17, and 18. These analyses showed the presence of the new carbonyl species, formed in the reaction between the isocyanate and blocked polyamine compositions.

What is claimed is:

1. Modified organic isocyanate composition containing urea and/or biuret groups and/or salts of these groups, obtained from the reaction of a blocked polyamine composition and an unblocked polyisocyanate composition, said blocked polyamine composition being obtained from the reaction of:
   (a) a polyamine composition containing primary and/or secondary amino groups and having a number averaged amine functionality of at least 1.0; and
   (b) a suitable blocking agent, wherein the reaction of said blocked polyamine composition with aid unblocked polyisocyanate composition proceeds more slowly relative to the reaction of the corresponding free polyamine composition with said unblocked polyisocyanate composition;
said polyisocyanate composition consisting essentially of carbocyclic aromatic organic polyisocyanates having a reactive isocyanate functionality of at least 1.0 and wherein the isocyanate groups of said aromatic organic polyisocyanates are attached directly to aromatic rings; wherein the blocked polyamine and the polyisocyanate are combined at a temperature of not more than 50° C.

2. Modified organic isocyanate composition of claim 1 wherein said reaction between said blocked polyamine and polyisocyanate is conducted so as to provide an excess of isocyanate groups over the sum total of the blocked polyamine groups of at least 1:5:1.0.

3. Modified organic isocyanate composition of claim 1 wherien the primary and/or secondary organic amine containing composition has a number averaged amine functionality of from about 0.1 to about 2.0 and which contains one or more ingredients having amine (primary and secondary functionality of greater than 2.

4. A composition according to claim 2 wherein the ratio of isocyanate and/or isothiocyanate groups to the sum total of all blocked (primary and/or secondary) amine groups and/or all Zerewitinoff active hydrogen groups, in the blocked polyamine composition, is at least 3:1.

5. A composition according to claim 2 wherein the ratio of isocyanate and/or isothiocyanate groups to the sum total of all blocked (primary and/or secondary) amine groups and/or all Zerewitinoff active hydrogen groups, in the blocked polyamine composition, is at least 5:1.

6. A process for preparing the modified isocyanate compositions of claim 1 wherein the reaction between the polyamine composition and the polyisocyanate are conducted in bulk.

7. A process for preparing the modified isocyanate compositions of claim 1 wherein the reaction between the polyamine composition and the polyisocyanate is conducted in the presence of a solvent which is substantially free of isocyanate reactive groups or impurities.

8. A process for preparing the modified isocyanate compositions of claim 1 wherein the reaction between the polyamine composition and the polyisocyanate is conducted using a continuous in-line mixing or impingment mixing apparatus.

9. A modified isocyanate composition prepared according to claim 1 wherein the blocked polyamine composition is selected from the group consisting of carbamic acids, salts thereof, and mixtures of said carbamic acids and/or salts with unreacted polyamines.

10. A modified isocyanate composition prepared according to claim 1 wherein the blocking agent used to prepare the blocked polyamine composition is carbon dioxide.

11. A modified isocyanate composition prepared according to claim 1 wherein the blocking agent used to prepare the blocked polyamine composition is carbon disulfide.

12. A modified isocyanate composition prepared according to claim 1 wherein the blocking agent used to prepare the blocked polyamine composition is a hydrohalic acid.

13. A modified isocyanate composition prepared according to claim 1 wherein the blocking agent used to prepare the blocked polyamine composition is anhydrous hydrochloric acid.

14. A modified isocyanate composition prepared according to claim 1 wherein the blocking agent used to prepare the blocked polyamine composition is a carboxylic acid.

15. A modified isocyanate composition prepared according to claim 1 wherein the blocking agent used to prepare the blocked polyamine composition is an organic sulfonic acid.

16. A modified isocyanate composition prepared according to claim 1 wherein the blocking agent used to prepare the blocked polyamine composition is a polycarboxylic acid, or mixture of polycarboxylic acids, having a number averaged carboxylic acid functionality of at least 2.0 and a carboxylic acid equivalent weight of at least 50.

17. A modified isocyanate composition prepared according to claim 1 wherein the blocking agent used to prepare the blocked polyamine composition is a polycarboxylic acid, or mixture of polycarboxylic acids, having a number averaged carboxylic acid functionality of at least 2.0 and a carboxylic acid equivalent weight of at least 100.

18. A modified isocyanate composition prepared according to claim 1 wherein the blocking agent used to prepare the blocked polyamine composition is selected from the group consisting of adipic acid, trifluoroacetic acid, trichloroacetic acid, isophthalic acid, terephthalic acid, benzoic acid, isomers of monohalobenzoic acids, isomers of dihalobenzoic acids, isomers of trihalobenzoic acids, isomers of nitrobenzoic acids, isomers of dinitrobenzoic acids, isomers of trinitrobenzoic acids, and mixtures thereof.

19. A modified isocyanate composition prepared according to claim 1 wherein the blocking agent used to prepare the blocked polyamine composition is an aromatic polycarboxylic acid, or mixture of aromatic polycarboxylic acids, having a number averaged carboxylic acid functionality of at least 2.0, a carboxylic acid equivalent weight of at least 65, and wherein substantially all of the carboxylic acid groups are bonded directly to an aromatic ring via the carbonyl carbon atom of the group.

20. A modified isocyanate composition prepared according to claim 1 wherein the blocked polyamine composition is selected from the group consisting of ammonium carboxylate salts, mixtures of said salts with unreacted polyamines and mixtures of said salts with organic carboxylic acids.

21. A modified isocyanate composition prepared according to claim 1 wherein the blocked polyamine composition is selected from the group consisting of ammonium sulfonate salts, mixtures of said salts with unreacted polyamines and mixtures of said salts with organic sulfonic acids.

22. A modified isocyanate composition prepared according to claim 1 wherein the blocked polyamine composition is selected from the group consisting of ammonium hydrochloride salts and mixtures of said salts with unreacted polyamines.

23. A modified isocyanate composition prepared according to claim 1 wherein the blocked polyamine composition is selected from the group consisting of mono(trialkylsilyl)derivatives of primary amines and mixtures of these derivatives with unreacted polyamines.

24. A modified isocyanate composition prepared according to claim 1 wherein the blocking agent used to prepare the blocked polyamine composition is the reactive precursor to a trialkylsilyl group and/or the reactive precursor to a triarylsilyl group.

25. A modified isocyanate composition prepared according to claim 1 wherein the blocking agent used to prepare the blocked polyamine composition is an $\alpha,\beta$-unsaturated mono or polycarboxylic acid, any ester of an $\alpha,\beta$-unsaturated mono or polycarboxylic acid, any amide of an $\alpha,\beta$-unsaturated mono or polycarboxylic acid, $\alpha,\beta$-unsaturated mono or polynitrile, $\alpha,\beta$-unsaturated mono or polysulfone, and an $\alpha,\beta$-unsaturated mono or polysulfoxide.

26. A modified isocyanate composition prepared according to claim 1 wherein the blocking agent used to prepare the blocked polyamine composition is a tertiary alkyl or aralkyl halide, sulfate diester, or sulfonate ester.

27. A modified isocyanate composition prepared according to claim 1 wherein the blocking agent used to prepare the blocked polyamine composition is selected from the group consisting of triarylboron compounds; trialkyl, triaryl, aralkyl borates; halides, nitrates, carboxylates, sulfates or sulfonates of zinc, iron magnesium, calcium, copper, cobalt, nickel, lead, mercury, tin, manganese, silver, barium, bismuth, lithium, selenium, or silicon and mixtures thereof.

28. A modified isocaynate composition prepared according to claim 1 wherein the polyisocyanate contains aromatic isocyanates in which some portion of the reactive isocyanate groups are bonded direclty to an aromatic ring.

29. A composition according to claim 28 in which the polisocyanate contains on or more isomers of toluene diisocyanate.

30. A composition according to claim 28 in which the polyisocyanate contains one or more isomers of diphenylmethane diisocyanate.

31. A composition according to claim 30 in which the polyisocyanate contains at least 50 mole percent 4,4'-diphenylmethane diisocyanate; 2,4'-diphenylmethane diisocyanate; 2,2'-diphenylmethane diisocyaante; or mixtures thereof.

32. A composition according to claim 30 in which the polyisocyanate contains at least 95 mole percent 4,4'-diphenylmethane diisocyanate; 2,4'-diphenylmethane diisocyanate; 2,2'-diphenylmethane diisocyanate; or mixtures thereof.

33. A composition according to claim 31 in which the diphenylmethane diisocyanate constituent contains at least 10 mole percent of the 2,4'-isomer.

34. A composition according to claim 1 wherein the polyamine of the blocked polyamine composition is a polyether obtained from the reaction of propylene oxide, ethylene oxide, or mixtures thereof, with a suitable initiator; followed by ammination.

35. A composition according to claim 1 wherein the polyamine of the blocked polyamine composition is a polyether obtained from the reaction of propylene oxide with a suitable initiator; followed by ammination.

36. A composition according to claim 1 wherein the reactive, primary and secondary, amine equivalent weight of the polyamine to the blocked polyamine composition is at least 100.

37. A composition according to claim 1 wherein the reactive, primary and secondary, amine equivalent weight of the polyamine precursor to the blocked polyamine composition is at least 250.

38. A composition according to claim 1 wherein the reactive, primary and secondary, amine equivalent weight of the polymaine to the blocked polyamine composition is at least 1000.

39. A modified isocyanate composition of claim 38 which is liquid, substantially homogeneous, and free of solids or gross phase separation after standing for at least 7 days at a temperature of not more than 23° C. under an inert atmosphere.

40. A modified isocyanate composition of claim 39 which has a number averaged isocyanate functionality of from 1.9 to 2.2.

41. A modified isocyanate composition of claim 40 which is free of urethane groups.

42. Modified organic isocyanate composition of claim 51 wherein the polyamine containing composition has a number averaged amine functionality of at least 2.0.

43. Modified organic isocyanate composition of claim 50 wherein said suitable blocking agent is selected from the group consisting of proton acids, Lewis acids, silylating agents, metalating agents, or alkylating agents.

* * * * *